United States Patent [19]

Okamoto et al.

[11] Patent Number: 5,705,346
[45] Date of Patent: Jan. 6, 1998

[54] METHOD FOR DETECTING A TARGET NUCLEIC ACID BY USING AN INTERACTION OF TWO KINDS OF REAGENTS

[75] Inventors: Tadashi Okamoto, Yokohama; Yoshinori Tomida, Atsugi; Nobuko Yamamoto, Isehara; Masahiro Kawaguchi, Atsugi; Keisuke Makino; Akira Murakami, both of Kyoto, all of Japan

[73] Assignee: Canon Kabushiki Kaisha, Tokyo, Japan

[21] Appl. No.: 671,829

[22] Filed: Jun. 25, 1996

Related U.S. Application Data

[63] Continuation of Ser. No. 157,427, Nov. 26, 1993, abandoned.

[30] Foreign Application Priority Data

Nov. 27, 1992  [JP]  Japan ................................. 4-318958

[51] Int. Cl.$^6$ ................................................. C12Q 1/68
[52] U.S. Cl. ................... 435/6; 435/810; 436/501; 536/23.1; 536/24.1; 536/24.3; 536/24.31; 536/24.32; 536/24.33; 935/77; 935/78
[58] Field of Search ...................... 435/6, 810; 436/501; 536/23.1, 24.1, 24.3–24.33; 935/77, 78

[56] References Cited

FOREIGN PATENT DOCUMENTS

| 0229943 | 7/1987 | European Pat. Off. | C12Q 1/68 |
| 0232967 | 8/1987 | European Pat. Off. | C12Q 1/68 |
| 0320308 | 6/1989 | European Pat. Off. | C12Q 1/68 |
| 0455517 | 11/1991 | European Pat. Off. | C12Q 1/68 |
| WO89-10415 | 11/1989 | WIPO | C12Q 1/68 |

OTHER PUBLICATIONS

Cardullo, et al. Detection of nucleic acid hybridization by nonradiatibe fluorescence resonance energy transfer, Proc. Natl. Acad. Sci–USA (Dec. 1988) 85:8790–8794.

Shimidzu, et al. Syntheses of oligonucleotide derivatives with P(V) porphyrin and their properties, (Nov. 11–13, 1992) 27:97–98.

Comprehensive Dictionary of Physical Chemistry, L. Ulicky and T. J. Kemp ed. Ellis Horwood Publisher p. 103.

Purugganan, et al. Accelerated Electron Transfer Between Metal Complexes Mediated by DNA. Science (23. Sep. 1988) 241:1645–1649.

Rahman., et al. Complexes involving quercetin, DNA and Cu(II), Carcinognesis (1990) 11:2001–2003.

Strobel et al. Preparation and Characterization of Spin–Labeled Oligonucleotides for DNA Hybridization, Bioconj. Chem (1991) 2:89–95.

Cullis et al. Electorn Conduction and Trapping in DNA: An Electron Spin Resonance Study. J. Chem. Soc. Faraday Trans. (1990) 86:591–592.

Morrison, et al.; "Solution phase . . . " Anal. Biochem; vol. 183, pp. 231–244, 1989.

Brun, et al.; "Dynamics of . . . ", JACS, vol. 114, pp. 3656–3660, 1992.

Fromherz, et al.; "Photoinduced . . . " JACS, vol. 108, pp. 5361–5362, 1986.

Primary Examiner—Ardin H. Marschel
Attorney, Agent, or Firm—Fitzpatrick, Cella, Harper & Scinto

[57] ABSTRACT

A method for detecting a target nucleic acid comprises the steps of reacting a sample with a probe in the presence of two or more kinds of reagents capable of being made an irreversible change capable of being detected and accumulating by an interaction through a double helix structure under a condition enabling the replication of the formation and dissociation of a hybrid composed of the target nucleic acid in the sample and the probe, accumulating the irreversible change caused by the interaction of the reagents, and then detecting the accumulated change.

30 Claims, 2 Drawing Sheets

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:1:

GTTGTAAAAC GACGGCCAGT    20

( 2 ) INFORMATION FOR SEQ ID NO:2:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:2:

```
GTTGTAAAAG GACGGCCAGT          20
```

METHOD FOR DETECTING A TARGET NUCLEIC ACID BY USING AN INTERACTION OF TWO KINDS OF REAGENTS

This application is a continuation of application Ser. No. 08/157,427 filed Nov. 26, 1993, now abandoned.

BACKGROUND OF THE INVENTION

1. Field of the Invention

The present invention relates to a method for detecting or identifying a desired base sequence of a nucleic acid (DNA or RNA) of a virus, a microorganism, an animal, a plant or a man, or a method for detecting the presence or absence of a variant in the base sequence, and a probe for use in the method.

2. Related Background Art

Many varied genes have been found owing to the development of the analytical techniques with of nucleic acids, and various kinds of hereditary diseases based on the variation of genes are being elucidated. It is now apparent that in such hereditary diseases, the bases of the gene are partially deleted, or the point mutation of the bases occurs, so that the protien encoded by a gene varies and various symptoms appear. At present, these hereditary diseases are mainly identified by assays using enzymatic or immunological techniques using an antibody after the symptoms appear. However, from the viewpoint of early treatment, it is important to identify the presence of the gene variant before serious symptoms appear.

Examples of techniques for detecting the change of DNA or RNA of such a varied gene are the RFLP (restriction fragment length polymorphism) method and a method for determining the base sequence of DNA. However, when such a disease as mentioned above is diagnosed, tens to several thousand copies of DNA or RNA are only obtained occasionally, and in the RFLP and the base sequence determination method, one cannot expect a sufficiently high sensitivity as to detect a small number of the DNA or RNA copies.

In recent years, there have been suggested several methods by which DNA or RNA can be detected even from a small number of copies, but they have not been put to practical use because of a low S/N ratio or poor reliability. Therefore, at present, when DNA or RNA is detected on the basis of a small number of copies, it is conventional to increase, i.e., amplify, the target DNA or RNA.

As a means for amplifying DNA or RNA, a PCR (polymerase chain reaction) method is now widely utilized. For example, the amplification of DNA by the PCR method is carried out as follows:

(1) Two kinds of oligonucleotide primers of about 20-mer are prepared. These primers are complementary to the 5' side of each chain of a target double-strand DNA having about 200 base pairs and containing a base sequence to be detected therein.

(2) In about 100 μl of a suitable buffer solution there are dissolved the target DNA, the above-mentioned two kinds of oligonucleotide primers (100 pmol, respectively) and deoxynucleotide triphosphoric acids (1.25 mM, respectively) of four kinds of bases (adenine, guanine, cytosine and thymine).

(3) The solution is heated at 94° C. for 5 minutes to denature the target double-strand DNA.

(4) 10 units of a heat-resistant DNA polymerase (e.g., Taq NDA polymerase) are added to the solution.

(5) Annealing is conducted at 50° C. for 2 minutes.

(6) A polymerization reaction is carried out at 72° C. for 3 minutes.

(7) The above-mentioned steps (3) to (6) [except the step (4)] are repeated as required (25 to 30 cycles).

(8) The amplified DNA is extracted by a suitable treatment.

The thus amplified DNA is detected and analyzed by the above-mentioned RFLP, base sequence determination method, or the like.

As described above, according to the PCR method, a trace amount of a nucleic acid not detected by a conventional detection technique is amplified, whereby such detection is made possible. However, this method also has the following problems.

(1) The amplification and the detection are carried out by the completely different means. Accordingly, a sequential operation of the amplification, the extraction of nucleic acid and detection is required until the final detection, which takes much labor and much time.

(2) The ease of the polymerization depends upon the base sequence, the length and the like of the primer, and, in certain cases, the polymerization does not proceed at all or the polymerization rate is extremely low. Furthermore, unnecessary amplification is carried out owing to the mispriming of the primer. The reasons for these phenomena are not completely understood, but it can be postulated that they are concerned with the fact that the polymerization reaction is conducted with the aid of an enzyme. Therefore, in order to select the primer, many experiments involving trial and error are often required.

(3) A temperature cycle is used for the amplification, and thus, in order to change a temperature difference of 40° C. or more at a high velocity, a device capable of programming the temperature with respect to time is necessary. Specifically, a heater and a cooler having a large capacity are necessary, which leads to an increase of cost.

(4) In compliance with the demands of a detecting system, the nucleic acid portion of 200 or more bases is amplified. However, PCR cannot amplify the nucleic acid portion of 20 to 30 bases in principle. However, a certain disease can be specified sufficiently by recognizing the sequence of about 20 bases in certain cases. If the PCR method is used for such a case, the nucleic acid portion is excessively amplified, which leads to the loss of time and the waste of expensive reagents.

SUMMARY OF THE INVENTION

In view of the above-mentioned problems of conventional techniques, the present invention has been intended, and an object of the present invention is to provide a method for detecting a target nucleic acid. According to the detecting method of the present invention, a small amount of a sample can be detected efficiently in one system under easily controllable reaction conditions without a prior amplification of the target nucleic acid, and thus the detecting method of the present invention is suitable for the analysis of a trace amount of the sample.

Another object of the present invention is to provide a method for detecting a target nucleic acid which permits analysis at a low cost by the use of a simply constituted apparatus.

The above-mentioned objects can be achieved by the present invention.

That is, the present invention is directed to a method for detecting a target nucleic acid which comprises the steps of reacting a sample with a probe in the presence of two or more reagents wherein an irreversible signal change occurs as a result of the interaction of two reagents with the double helix structure, under conditions wherein an equilibrium exists between formation and dissociation of a hybrid composed of the target nucleic acid in the sample and the probe, accumulating the irreversible change caused by the interaction of the reagents, and then detecting the accumulated change.

BRIEF DESCRIPTION OF THE DRAWINGS

In this drawing, □ indicates a case where a probe, a target DNA and fluorescein were contained in a reaction system and light irradiation was carried out; ■ indicates a case where the probe, the target DNA and fluorescein were contained in the reaction system and the light irradiation was not carried out; and ♦ indicates a case where the probe and fluorescein were contained in the reaction system and the light irradiation was carried out.

In this drawing, □ indicates a case where a probe having both bonded terminals, a target DNA and fluorescein were contained in a reaction system and light irradiation was carried out; ■ indicates a case where the probe having both bonded terminals, the target DNA and fluorescein were contained in the reaction system and the light irradiation was not carried out; and ♦ indicates a case where the probe having both bonded terminals and fluorescein were contained in the reaction system and the light irradiation was carried out.

DESCRIPTION OF THE PREFERRED EMBODIMENTS

A detection method of the present invention is based on a principle which is quite different from conventional techniques, and it comprises detecting a double helix structure itself which a hybrid has, and then amplifying the detected signal. That is, the present invention is substantially different from a conventional method such as a PCR method in which a step of amplifying the number of copies of a target nucleic acid and a step of detecting the amplified target nuclei acid are separately carried out. In the present invention, the detected signal of the double helix structure is amplified, and so the amplification and the detection are made in one system, and effective analysis can be achieved by a simpler device at a low cost.

Furthermore, since the method of the present invention intends to detect the formation of the double helix structure in forming a hybrid, then according to the present invention, it is unnecessary to separate excessive probes from the hybrid of the probe and the target nucleic acid (B/F separation). In the present invention, the formation of the desired nucleic acid hybrid can be detected by setting conditions for precisely detecting the double helix structure alone, even if a nonspecific adsorption or a mismatch is present, and thus the present invention can improve the precision of the measurement.

The present invention can be applied to the formation of the double helix structure such as DNA-DNA hybridization or DNA-RNA hybridization.

Now, the present invention will be described in detail.

A phenomenon called hybridization has been heretofore considered only to be based on a hydrogen bond between the mutually complementary bases of a nucleic acid, because in general, after the immobilization of the nucleic acid (DNA or RNA), a hybridization reaction is carried out. However, in the case of the hybridization reaction in a solution, the formation of the double helix structure can be expected, if the nucleic acid forms double strands having a certain length. The present inventors have paid much attention to the fact that the nucleic acid having a single strand is different from the nucleic acid having double strands (the hybrid) in a higher-order structure and chemical properties, and its detection system has been established. In consequence, the present invention has been completed.

In the double helix structure, the base portion of the nucleic acid forms a base pair by a hydrogen bond, and the helix of the nucleic acid is wound, wherein a phosphorus portion and a saccharide portion are outwardly oriented. The nucleic acid bases are mutually stacked to be stabilized, and positioned at the center of a helix axis. As types of double helix structure, A, B, C and Z types and their variants are known. These structures are different not only in the base sequence but also in a pitch length, the symmetry of the helix, the width of a groove, the depth of the groove and the like under the influence of a specific kind of ion or a salt concentration used at the time of annealing. Even if the same base sequence is used, it is considered that the double helix structures vary based on the conditions employed. In general, DNA takes the B type structure, and in this case, the pitch length is 33.8 Å and the number of the nucleic acid base pairs per pitch is 10 bases.

The present invention is directed to a method for detecting the formation of a double helix structure by using reagents capable of generating a detectable change by the utilization of the double helix structure which the hybrid possesses, and then measuring the chemical change of the reagents.

As the reagents, there can be utilized 2 or more kinds of reagents by which an interaction is brought about through the double helix structure to generate a detectable irreversible change.

In the method of the present invention, the reagents are allowed to coexist with a reaction system of a sample and a probe. A target nucleic acid contained in the sample and the probe are reacted under conditions under which formation and dissociation of the hybrid are repeated. Afterward, the resulting accumulated (amplified) detectable signal is detected.

Next, the method of the present invention will be described in reference to a typical example in which the transfer of an electric charge is employed as the interaction.

For example, as the reagents, there can be used an electron donor and an electron acceptor which carry out the electric charge transfer through the double helix structure, and the electron donor and the electron acceptor can be bonded to both the ends of the probe, respectively. In this case, the electron donor and the electron acceptor must be combined so that at least one of them may give rise to the detectable change which does not disappear as a result of the interaction (the electric charge transfer).

When the two kinds of reagents (the electron donor and the electron acceptor) are reacted with the sample, the electric charge transfer takes place between the electron donor and the electron acceptor through the double helix structure of the hybrid of the probe and the target nucleic acid. Such a hybrid is formed in case the target nucleic acid is present in the sample. As a result of the electric charge transfer, in at least one of the electron donor and the electron acceptor, a detectable change occurs. Next, this reaction system is exposed to conditions for dissociating the formed hybrid, so that the target nucleic acid is in the free state again. On the other hand, at this time, the detectable change by the interaction of the reagents which are bonded to the probe dissociated from the hybrid is fixed, because the detectable change is irreversible. Afterward, the reaction system in such a state is exposed to conditions for forming the hybrid again, and at this time, the target nucleic acid is reacted with the probe to which the electron donor and the electron acceptor which have not taken part in the interaction are bonded. As a result, the double helix structure is formed, and the interaction occurs between the electron donor and the electron acceptor through the thus formed double helix structure, so that at least one of the electron donor and the electron acceptor gives rise to the detectable change. Furthermore, since the formation of the hybrid and its dissociation are repeatedly carried out, the target nucleic acid catalytically functions to successively bring about the interaction of the reagents bonded to the probe. In consequence, the number of molecules of molecular the reagent involved with the detectable change can be increased, and the analytical signal can be amplified.

As described above, the present invention intends to amplify the detection signal instead of the target nucleic acid, and therefore, even if the target nucleic acid is present in a trace amount, the analysis can be achieved with a good sensitivity. Moreover, since it is not necessary to amplify the target nucleic acid, various kinds of expensive reagents required to amplify the target nucleic acid are unnecessary. In addition, in contrast to using a PCR method in which the step of amplifying the target nucleic acid and the step of detecting the amplified target nucleic acid are separately carried out, the amplification and the detection can be done in one system, which can simplify the analytical step.

In order to repeat the formation and the dissociation of the hybrid in the method of the present invention, various techniques can be utilized. For example, temperature conditions by which the formation and the dissociation of the hybrid are equilibrated can be used to obtain the repeating reaction.

Regarding the temperature conditions to be selected, they depend upon the length of the probe or the target nucleic acid, the salt concentration in the solution and so forth and whether this equilibrium condition slants to a single-strand side or a double-strand side. In general, the equilibrium state slants to the double-strand state at a low temperature (30° C. or less), and it slants to the single-strand state at a high temperature (70° C). However, from the viewpoint of the good efficiency of the amplification, it is preferable to employ the temperature of a melting point of the nucleic acid at which the change of the nucleic acid between the single strand and the double strand is most rapidly carried out, a neighborhood of the melting point, or suitably a temperature in the range of ±5° C. of the melting point.

In measuring the melting point of the nucleic acid, an error is often unavoidable. Accordingly, there is a gap between the set melting point and the actual melting point occasionally. Furthermore, in the long nucleic acid, the higher-order structure of its base sequence gives rise to a difference between the measured and set melting point and the actual melting point sometimes. In order to avoid the disturbance of the amplification effect caused by such an error, or in order to stably initiate the change between the single-strand state and the double-strand state, the temperature may be allowed to fluctuate within a certain temperature range of the melting point of the nucleic acid, suitably within a temperature range of ±5° C. of the melting point.

When the electric charge transfer is utilized as the interaction, as described above, the reagents are not limited to the electron donor and the electron acceptor, and at least a pair of the electron donor and the electron acceptor may be contained in the reaction system. The interaction between both of the electron donor and the electron acceptor is detected as the change of a chemical structure, the change of an electron state of the electron donor, the electron acceptor or a third substance which can interact with it, or the change of the signal attributed to the changed substance before and after the formation of the hybrid.

A relation between the electron donor and the electron acceptor which is referred to in the present invention is decided by a relation between energy states of both. Therefore, in the present invention, the substance generally defined as the electron donor or the electron acceptor is not used as thus defined, and substances which can become the electron donor and the electron acceptor are selectively used in combinations of two or more kinds of reagents. For example, anthracene is utilized as the typical electron donor and its oxidation-reduction potential has been measured. On the other hand, it is well known that characteristics of anthracene have also been evaluated as an electron acceptor.

In evaluating the interaction of the electron donor and the electron acceptor, the so-called through space and through bond are considered. The former includes, for example, a case where the electron donor and the electron acceptor interact through the stacked base pair of the nucleic acid, and a case where the interaction is based on a proximity effect of the electron donor and the electron acceptor with the change toward the double helix structure. As the latter (the through bond), there can be considered the transfer of an electric charge through the bases, the phosphorus portion and the saccharide portion constituting the nucleic acid. In either case, no restriction is put on the conformation of the interaction, so long as the interaction of the electron donor and the electron acceptor is attributed to the formation of the double helix.

The interaction of the electron donor and the electron acceptor via the stacked bases of the nucleic acid can be achieved as follows. When the electron donor and the electron acceptor placed at a position where they react with the double helix structure are separated from each other sufficiently such that the interaction cannot be naturally carried out, an electron released from the electron donor is successively delivered from the base to the adjacent base through an electron cloud spread on the base pair of the nucleic acid, until it finally reaches the electron acceptor. Another mechanism can be considered in which the electron acceptor conversely draws an electron from the base pair of the nucleic acid and this behavior is carried out in succession, and finally the electron is taken from the electron donor. In short, a mediator in the electric charge transfer is the base pair of the nucleic acid.

To the contrary, the interaction based on the proximity effect of the electron donor and the electron acceptor can be carried out in a case where the electron donor and the electron acceptor get sufficiently close to each other to permit the interaction owing to the formation of the double-stand structure. For example, if both of the electron donor and the electron acceptor are bonded to the probe and this probe is in the single stranded state they do not interact, and if the probe is hybridized with the target nucleic acid to form the double helix structure and thereby cause the electron donor and the electron acceptor to move closer to each other, the interaction takes place. Therefore, the formation of the double helix structure can be detected by the occurrence of the interaction.

Incidentally, when the achievement of the electric charge transfer is difficult between the electron donor and the electron acceptor via the double helix structure, a substance called a mediator or a sensitizer which can mediate the electric charge transfer therebetween may be interposed.

As described above, it is necessary that the electron donor and the electron acceptor are placed at a position where they react with the double helix structure to carry out the interaction therebetween. In order to place the reagents at the position where they react with the double helix structure, they may be inserted between the base pair of the nucleic acid as an intercalater, buried in the groove of the double helix structure, or disposed so as to snuggle to the double helix structure. In any case, it is essential to the present invention that they are specifically placed to the double helix structure of the hybrid formed from the single strand probe and the target nucleic acid.

Above all, the intercalater embodiment is most advantageous when the electric charge transfer via the stacked base pairs is utilized. That is, the intercalater is usually a lamellar compound having a spread electron cloud, and it is arranged on an extended line of the stacked base pairs of the nucleic acid, at the same distance as the distance between the base pairs of the nucleic acid, and in parallel with the base pairs of the nucleic acid. For example, if the intercalater as the electron donor and the electron acceptor are arranged on the opposite sides of the double helix structure, the electron released from the electron donor is delivered from the base to the adjacent base through each electron cloud of the base pairs of the nucleic acid, so that the electron straight streams toward the electron acceptor. Alternatively, if the intercalater as the electron acceptor and the electron donor are arranged on the opposite sides of the double helix structure, an electron hole of the electron acceptor conversely draws an electron from the adjacent base pair of the nucleic acid and this electron drawing behavior is carried out in succession between the other base pairs of the nucleic acid, and finally the electron is taken from the electron donor to terminate the electric charge transfer. In view of these mechanisms, in the case of the electric charge transfer via the stacked base pairs, it is preferable that at least one of the electron donor and the electron acceptor is the intercalater, and it is more preferable that both of them are the intercalators, because the efficiency of the electric charge transfer can be improved.

As a technique for detecting the change of the interaction of two or more kinds of reagents which is caused by the formation of the double helix structure, there is a method for detecting the change of the electron acceptor. This method can be classified into several categories in compliance with detecting means.

For example, the transferred electric charge can be observed as a spectrum change in accordance with a spin decoupling method using a spin labelling agent by ESR or the like. Alternatively, the transferred electric charge can be observed as the appearance or the change of a new absorption spectrum, as an electric charge transfer absorption band. In a system in which a solution is colored or discolored as a result of the electric charge transfer, the change can be directly observed with the naked eye, and it is further effective as the simple system. A luminescent system such as fluorescence or phosphorescence can also be utilized. In this case, there can be utilized a reaction by which fluorescence or phosphorescence is freshly generated, or a reaction in which the luminescence disappears as a result of the interaction. Alternatively, another method can be utilized in which the electron acceptor is chemically converted into another substance as a result of the electric charge transfer, and this converted substance is then detected. In this case, a third substance can be added to the converted substance to generate chemical luminescence by the chemical reaction between both the substances. When a protein such as an enzyme or an antibody is utilized as the third substance, a detection method using biological luminescence is utilizable.

The detection of the interaction may be achieved by detecting the change of the electron donor in addition to the change of the electron acceptor. Fundamentally, most of the methods for detecting the change of the electron acceptor can be directly applied. When a fluorescent substance is used as the electron donor, a direct change such as the disappearance of fluorescence can be detected by the utilization of the fact that the quantum yield of the fluorescence is decreased by the electric charge transfer, or alternatively, such change may be combined with some reactions so as to permit detection with the naked eye.

In the present invention, the electron donor can be activated by light to release an electron and the electric charge transfer can be then started. In addition to this manner, a third substance by which the electron donor may be stimulated to release the electron may be utilized.

Furthermore, in place of the electron donor, the electron acceptor may be activated to draw the electron from the electron donor. In this case, any initiator such as light may be used, as in the case of the electron donor.

As described above, a substance called a mediator or a sensitizer which can mediate the electric charge transfer may be interposed as the third substance in addition to the electron donor and the electron acceptor. This kind of substance interacts with the double helix to urge the electron donor or the electron acceptor not directly bonded to the double helix to do the electric charge transfer.

Needless to say, the non-bonded electron donor and electron acceptor which are free in a reaction system are also utilizable, so long as the interaction of both the free reagents specifically occurs only at a position where the double helix structure is present.

However, in a certain case, one or both of the electron donor and the electron acceptor are present in a free state in the reaction system, and the interaction occurs therebetween irrespective of presence/absence of the double helix structure, so that a background rises and an S/N ratio declines. In such a case, it is preferable that one or both of the electron donor and the electron acceptor are bonded to the probe, when used. If the rise of the background is inhibited by suitably selecting specific concentrations of these free reagents in the reaction system, the free reagents can be used at such concentrations. When the electron donor and/or the electron acceptor is bonded to the probe at the time of the utilization, the bonding of the electron donor and/or the electron acceptor to the probe is carried out via a linker such as $(CH_2)_n$, if necessary. In this case, the positional relation of the electron donor and the electron acceptor should be considered so that the interaction may be most effectively made.

The most suitable embodiment is a case where both of the electron donor and the electron acceptor are bonded to the probe as described above. In this case, the positional relation between the reagents for carrying out the interaction is definite, and therefore the control of the interaction can be advantageously achieved by regulating the positional relation of these reagents with respect to the probe. In this case, a distance between the electron donor and the electron acceptor on the probe can be suitably selected in compliance with the kinds of these reagents. When a vicinal effect is utilized, for example, when the interaction is obtained by the vicinal effect, the distance between the electron donor and the electron acceptor is preferably in the range of from 20 to 120 Å, more preferably from 50 to 80 Å. Furthermore, when the electric charge transfer is carried out via a double helix structure, the distance is preferably in the range of from 20 to 120 Å, more preferably from 50 to 80 Å. The positions of the probe to which the electron donor and the electron acceptor are bonded depend upon the length of the probe, but it is advantageous from the viewpoint of the facility of the bonding that they are separately bonded to both the ends of the probe.

The length of the probe is suitably selected so that a good hybridization with the target nucleic acid may be possible and a stable double helix structure may be obtained. However, when both of the electron donor and the electron acceptor are bonded to the probe and they are close to each other, the interaction occurs in a certain case, even if the double helix structure is not present. Thus, the length of the probe is decided in consideration of such a case. For example, the probe length is 8 or more bases, preferably 12 or more bases.

However, in addition to the length of the probe, the base sequence itself as well as a salt concentration and an ion intensity in the reaction system have a large influence on the stabilization of the double helix structure. A G-C base pair contains more hydrogen bonds than an A-T base pair, and therefore, in the sequence containing many G-C base pairs, the more stable double helix structure can be formed. It is considered that if the molar concentration of KCl is raised from 0.01M to 1M, the melting point of DNA rises as much as 30° C. In addition, the presence of the intercalator also largely contributes to the stability of the double helix structure. Therefore, the suitable utilization of these stabilizing factors permits the use of the probe having a length of less than the 8 bases.

Typical examples of the reagents which can be used in the present invention as follows:

Examples of the spin labelling agent include 4,4-dimethyloxazolidine-N-oxyl (DOXYL), its derivatives, 2,2, 5,5-tetramethylpyrrolidine-N-oxyl (PROXYL) and its derivatives, and 2,2,6,6-tetramethylpiperidine-N-oxyl (TEMPO) and its derivatives.

Examples of the fluorescent intercalator include acridine, anthracene, pyrene, ethidium bromide, pyrylium, proflavine, porphyrin, thiazole orange dimer (TOTO), oxazole yellow (YOYO), and derivatives thereof.

Examples of the other general fluorescent dyestuff include cyanine, azulene, trinuclear dyestuffs, dansyl, fluorescein, Eosine, Rhodamine and riboflavin.

These compounds can be suitably used as the electron donor, the electron acceptor and the mediator for the sake of the evaluation of oxidation-reduction potential and the like.

The method of the present invention has been described in reference to the case where the electron donor and the electron acceptor for carrying out the electric charge transfer are used as the reagents, but these reagents are not limited to substances for carrying out the interaction by the electric charge transfer. Thus, optional reagents can be utilized, so long as they can give rise to a detectable and irreversible change by the interaction via the double helix structure.

Now, the present invention will be described in detail in reference to examples, but the scope of the present invention should not be limited to these examples.

EXAMPLE 1

[1] Preparation of a 20-mer oligonucleotide probe combined with a spin labelling agent TEMPO (4-hydroxy-2,2, 6,6-tetramethylpiperidine)

(1) Synthesis of 4-aminohexylamino-2,2,6,6-tetramethylpiperidine-N-oxyl(4-aminohexylamino-TEMPO)

0.5 mmol of 4-oxo-TEMPO and 5 mmol of hexamethylenediamine dihydrochloride were dissolved in 30 ml of methanol, and 0.4 mmol of sodium cyanoborohydride and molecular sieves 3A were then added thereto. Afterward, the mixture was stirred at room temperature for 24 hours to react them. Next, the reaction solution was filtered through a glass filter to remove the molecular sieves, and the solvent was then removed from the filtrate under reduced pressure. To the thus obtained residue, 30 ml of 1-N hydrochloric acid was added, and it was then dissolved therein, followed by extraction with chloroform. The resulting chloroform phase was washed with water, and chloroform was then distilled off under reduced pressure. Afterward, water was added to the resulting residue, and insolubles were removed by filtration. The resulting filtrate was subjected to distillation under reduced pressure again to remove the solvent, thereby obtaining a reddish oily product.

(2) Synthesis of an oligonucleotide 20-mer oligonucleotide a base sequence of which is complementary to a portion of M13mp18DNA as a target DNA (a single strand) was synthesized with a 381A DNA automatic synthesizing device made by ABI Co., Ltd. In this case, a 5' terminal dimethoxytrityl group was removed on the automatic synthesizing device. Its base sequence was as follows:

5'-GTTGTAAAACGACGGCCAGT-3' SEQ ID No.:1

(3) Synthesis of a spin label oligonucleotide probe

The oligonucleotide (1 µmol) synthesized in the above-mentioned step (2) was transferred to a gas tight syringe, while bonded to a CPG support. The subsequent reactions were carried out in the syringe. Next, 1 ml of dioxane in which 50 mg of carbonyl-N,N'-diimidazol (CDI) was dissolved was added to the CPG support, and the solution was then allowed to stand at room temperature for 1 hour. After washing with dioxane and then drying under reduced pressure, a DMSO solution (0.4 ml of 0.2M) of 4-aminohexylamino-TEMPO was added, and the solution was allowed to stand at 55° C. for 24 hours, washed with DMSO, dioxane and methanol in this order, and then dried under reduced pressure.

The spin label oligonucleotide was cut out and the protective was eliminated with concentrated aqueous ammonia in an ordinary manner, followed by purification with RPLC.

[2] Formation reaction of a hybrid of a TEMPO probe and M13 mp 18 DNA 0.2 µM of an oligonucleotide probe having TEMPO prepared in the above-mentioned [1] and M13 mp 18 DNA (0.2 µM, made by Takara Shuzo Co., Ltd.) were heated up to 80° C. in 1 mM phosphorus buffer solution (pH=7.0)/145 mM NaCl/5 mM KCl, and the solution was then slowly cooled to a melting point (63° C.) of the hybrid, so that the probe and the target DNA were maintained in the equilibrium state of a single strand and a double strand. Next, fluorescein (made by Kodak Co., Ltd.) was added to this reaction solution so that a final concentration might be 10 μM, to prepare the same seven samples in all. These samples were kept up under conditions for maintaining the equilibrium state of the single strand and the double strand, i.e., at a constant temperature of 63° C., and they were irradiated with light of 490 nm for 0, 20, 40, 60, 80, 100 and 120 minutes by the following light irradiating device. Afterward, the samples were cooled to room temperature, and the measurement of ESR was then carried out.

Furthermore, the same procedure as described above was carried out except that M13 mp 18 DNA was not used, to prepare samples (probes alone) for the measurement of ESR spectrum, and the measurement of ESR was done in like manner.

[3] Measurement of ESR spectrum

The measurement of ESR spectrum in each of the samples was made by sweeping the sample every 20 minutes, and intensity ratio and line width were then measured. In the above-mentioned ESR measurement, a measuring device made by JEOL, Ltd. was used, and a flat cell made of artificial quartz was used.

The ESR measuring device and the light irradiating device were set as follows:

TABLE 1

| Frequency | 9.42 GHz |
|---|---|
| Modulation | 100 kHz, 0.1 mT |
| Field | 335 mT |
| Time Constant | 0.3 sec |
| Power | 10 mW |
| Sweep Time | 8 min |
| Receiver Gain | 1.25 × 1000 |
| Light irradiating device | |
| Monochrometer | 490 nm |
| Power supply | 88.5 V-89 V/22 A |

Figure 1:
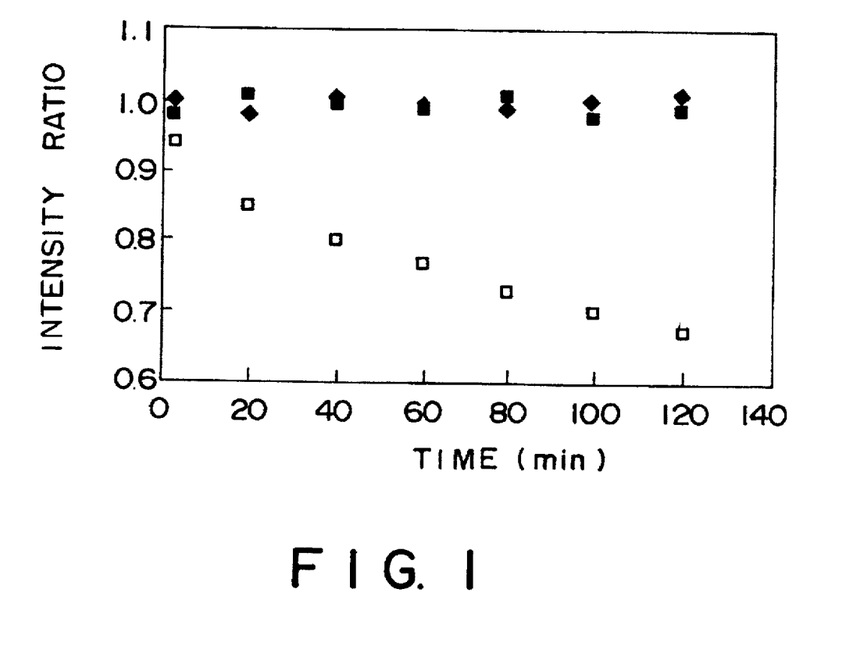
FIG. 1 is a graph showing the change with time of an ESR signal intensity ratio obtained in Example 1.

FIG. 1 shows a change with time of the ESR signal intensity in a case where a TEMPO-oligonucleotide probe alone was irradiated with light, a case where fluorescein/a TEMPO-oligonucleotide probe/M13 mp 18 DNA was irradiated with light, and a case where the light irradiation was not given. In addition, FIG. 2 shows a change with time of the line width of the ESR signal in the case that fluorescein/a TEMPO-oligonucleotide probe/M13 mp 18 DNA was irradiated with light.

Figure 2:
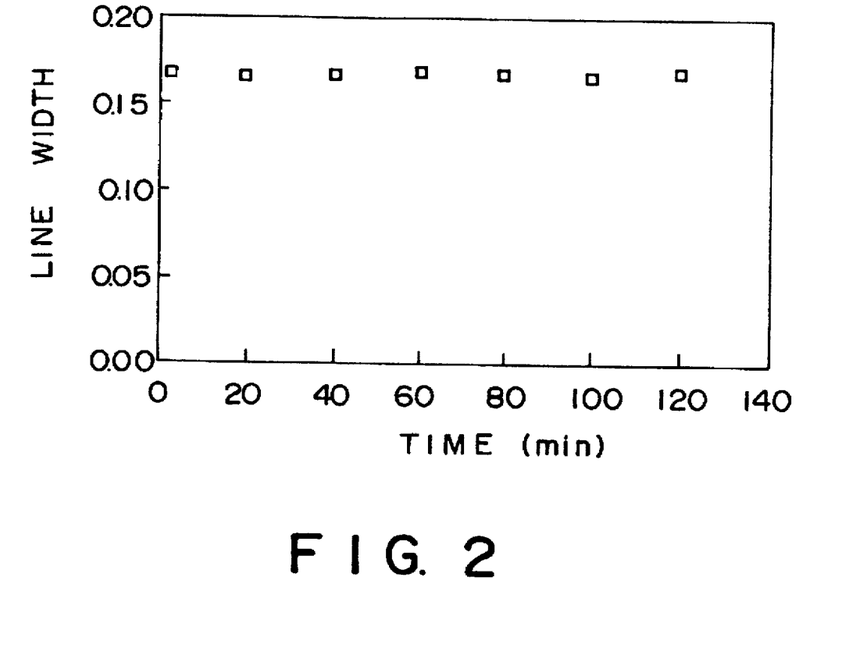
FIG. 2 is a graph showing the change with time of an ESR signal line width obtained in Example 1 in which the probe, the target DNA and fluorescein were contained in the reaction system and the light irradiation was carried out.
Figure 3:
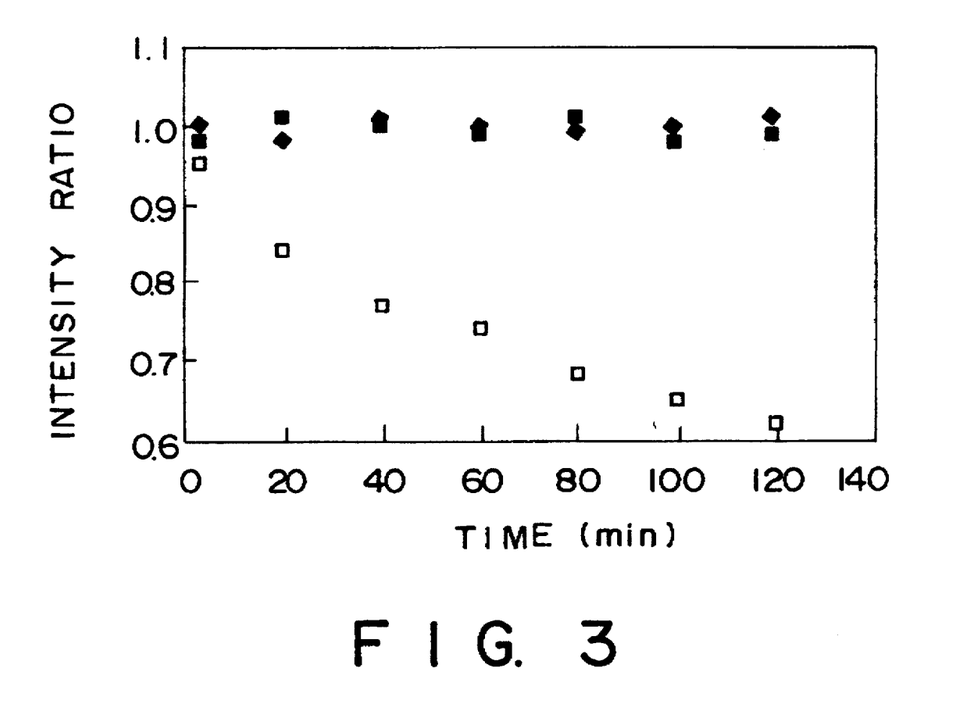
FIG. 3 is a graph showing the change with time of an ESR signal intensity ratio obtained in Example 3.

As understood from FIGS. 1 and 2, in the case of the TEMPO-oligonucleotide probe alone, the change of the intensity ratio was not observed, even when the light irradiation was carried out. Moreover, also in the case of fluorescein/the TEMPO-oligonucleotide probe/M13 mp 18 DNA, the change of the intensity ratio was not observed, when the light irradiation was not done.

On the contrary, in the case that fluorescein/the TEMPO-oligonucleotide probe/M13 mp 18 DNA was irradiated with light (490 nm), the intensity of ESR decreased with time (FIG. 1), and therefore the amount of TEMPO in which the spins were decoupled increased with time. Thus, it was confirmed that a detection signal was amplified. Furthermore, judging from the fact that any change of the line width was not observed (FIG. 2), it can be considered that the intensity change in ESR is not attributable to a chemical change. Accordingly, it can be understood that the spins of TEMPO were decoupled as a result of the transfer of the change from fluorescein to TEMPO via the probe/M13 DNA double strands, whereby the detection signal is amplified.

EXAMPLE 2

The same experiment as in Example 1 was carried out except that the following sequence was used as the base sequence of a probe:

5'-GTTGTAAAAGGACGGCCAGT-3' SEQ ID No.: 2

This sequence of the probe was that of the probe used in Example 1 in which the 10th base from the 5' terminal was changed from C to G, and therefore the probe sequence used in this example was different from that used in Example 1 in one base so as to mismatch with M13 mp 18 DNA.

To 0.2 μM of the probe having this mismatching sequence, 0.2 pM of M13 mp 18 DNA was added, and the solution was placed at a melting point by the same procedure as in Example 1. Next, fluorescein was added to the solution, and this solution was irradiated with light, and then cooled to room temperature. Afterward, changes with time of the intensity ratio and the line width of an ESR signal were inspected.

As a result, the intensity change seen in Example 1 was not observed, and the same intensity as in the case of the TEMPO-oligonucleotide probe alone was kept up. This fact indicates that a normal double-strand chain was not formed in a hybrid of the mismatching oligonucleotide probe and DNA, and an electric charge did not transfer, so that a signal was not amplified.

EXAMPLE 3

Synthesis of a (5'-TEMPO, 3'-FITC) oligonucleotide probe labeled at both terminals (1) Synthesis of an oligonucleotide combined with a 3'-amino group 20-mer oligonucleotide a base sequence of which is complementary to a portion of single strand M13mp18DNA as a model of the target DNA used in Example 1 was synthesized with 381A, made by ABI Co., Ltd., using 3'-aminomodifier CPG (1 μmol) made by Gren Research Co., Ltd. as a carrier. A 5' terminal dimethoxytrityl group was removed on the automatic synthesizing device.

(2) Synthesis of a spin label oligonucleotide probe

An oligonucleotide (1 μmol) synthesized in the above-mentioned step (1) was transferred to a gas tight syringe, while bonded to a CPG support. The subsequent reactions were carried out in the syringe. Next, 1 ml of dioxane in which 50 mg of carbonyl-N,N'-diimidazole (CDI) was dissolved was added to the CPG support, and the solution was then allowed to stand at room temperature for 1 hour. After washing with dioxane and then drying under reduced pressure, a DMSO solution (0.4 ml of 0.2M) of 4-aminohexylamino-TEMPO shown in Example 1 was added, and the solution was allowed to stand at 55° C. for 24 hours, washed with DMSO, dioxane and methanol in this order, and then dried under reduced pressure.

Next, the cut and deprotection of a spin label oligonucleotide were carried out with concentrated aqueous ammonia in an ordinary manner, followed by purification with RPLC, to obtain the spin label oligonucleotide in which TEMPO was labeled at a 5' terminal.

(3) Synthesis of an oligonucleotide probe labeled at both terminals

To the 3' terminal of a spin label oligonucleotide synthesized in the above-mentioned (2), a 3-amino-2-hydroxy group was bonded, and therefore the following operation was carried out to combine this amino group with FITC (fluorescein isothiocyanate, made by Sigma Co., Ltd.).

0.2 μmol (700 μl of aqueous solution) of the spin label oligonucleotide synthesized in the above-mentioned (2) was mixed with 100 μl of a 1M sodium carbonate buffer solution (pH=9), and a DMF solution containing 2 mg of FITC was added to the resulting solution and reaction was then carried out at 35° C. for 24 hours. Afterward, the reaction solution was treated by a gel filtration column NAP-25 made by Falmasia Co., Ltd. to remove a large excess of FITC, and then purified by RPLC to obtain a probe in which TEMPO was bonded to a 5' terminal and FITC was bonded to a 3' terminal.

(4) Measurement of ESR spectrum 0.2 μm of this probe and 0.2 pM of M13 mp 18 DNA were used, and the change with time of the intensity ratio and the line width of an ESR signal were inspected in the same manner as in Example 1. Between the probe alone and a hybrid of the light-unirradiated probe and a targe nucleic acid, any change of the intensity was not observed. On the contrary, only when the hybrid of the light-unirradiated probe and the targe nucleic acid was irradiated with light of 490 nm which was the excitation wave length of fluorescein, a signal was decreased with time, whereby the transfer of an electric charge could be confirmed (FIG. 2). Furthermore, the degree of spin decoupling was higher than in the case that fluorescein was not bonded to the probe, which meant that when the electron donor and the electron acceptor were bonded to both the terminals of the probe, the electron transfer took place more effectively, and in consequence, an effective signal amplification of the nucleic acid probe was attained.

EXAMPLE 4

An oligonucleotide (the same sequence as in Example 2) having a base sequence which was different from that of M13 DNA in one base in the middle of a probe was synthesized, and the same operation as in Example 3 was carried out to bond TEMPO and fluorescein to both the terminals of the probe.

After 0.2 μM of this probe and 0.2 pM of M13 mp 18 DNA were used in a usual manner, the change with time of the intensity ratio and the line width of an ESR signal were inspected in the same manner as in Example 1. Even when a probe/DNA composite was irradiated with light of 490 nm which was the excitation wave length of fluorescein, changes of the intensity of the ESR signal and the line width were not observed, as in the cases of the probe alone and the light-unirradiated probe/DNA composite.

According to the present invention, the detection of a double-stand structure by a nucleic acid probe can be carried out by amplifying a detection signal in one system, whereby a target nucleic acid can be detected with high sensitivity by a very simple operation.

Furthermore, since the amplification is carried out by a purely chemical reaction without utilizing an enzyme as in a PCR method, problems such as the incorrect amplification or the retardation of the amplification which are caused by an enzyme reaction can be avoided.

Particularly, in the case that the interaction of two or more substances is possible as a result of the transfer of an electric charge via the stacked bases of the nucleic acid, the effectuation of the amplification is affected by the presence of one mismatch in a base sequence, and in consequence, it is possible to detect the one mismatch.

Furthermore, since the scatter of a temperature at the time of the amplification is not present or, if any, about 5° C., an inexpensive device having a small capacity can be provided.

In addition, according to the present invention, the nucleic acid having 20 to 30 bases can be amplified in principle, and so the conventional problem that a short nucleic acid such as PCR cannot be amplified can be solved.

What is claimed is:

1. A method for detecting a target nucleic acid which comprises:
   (a) providing a sample containing a single stranded target nucleic acid having a specific base sequence;
   (b) providing a probe having a base sequence complementary to the specific base sequence;
   (c) forming a double-stranded hybrid between the target nucleic acid and the probe in the presence of two kinds of reagents both of which coexisting in the sample and being capable of interacting with each other through the double-stranded hybrid without direct physical contact between the two kinds of reagents to cause an irreversible detectable change in at least one of the reagents;
   (d) causing repeated formation and dissociation of the double stranded hybrid to generate the interaction between the two kinds of reagents which results in accumulations of irreversibly changed reagent which provides the detectable change; and
   (e) detecting the change provided from the accumulated irreversibly changed reagent to identify the target nucleic acid in the sample.

2. The method according to claim 1, wherein the step (d) is carried out by holding the sample under a condition that a temperature is fluctuated between points above and below a melting point of the target nucleic acid and probe.

3. The method according to claim 2, wherein the temperature is fluctuated within ±5° C. of the melting point.

4. The method according to claim 1, wherein the step (d) is carried out with a forward reaction of that in the double stranded hybrid is produced from the target and the probe, and with a back reaction of the double stranded hybrid is denatured to the target and the probe, being in equilibrium.

5. The method according to claim 4, wherein the step (d) is carried out by holding the sample under a predetermined temperature within ±5° C. of the melting point of the target nucleic acid and probe in the sample.

6. The method according to claim 5, wherein the predetermined temperature is the melting point.

7. The method for detecting a target nucleic acid according to claim 1, wherein the interaction between the two kinds of the reagents is accelerated by locating, through predetermined formation of the hybrid of the target nucleic acid and the probe, the two kinds of the reagents at a position where they are capable of interacting with each other.

8. The method for detecting a target nucleic acid according to claim 1, wherein the change by the interaction between the two kinds of the reagents is mediated by another material.

9. The method for detecting a target nucleic acid according to claim 1, wherein the irreversible change of the reagent is chemically detected.

10. The method for detecting a target nucleic acid according to claim 1, wherein the irreversible change of the reagent is optically detected.

11. The method for detecting a target nucleic acid according to claim 1, wherein the irreversible change by the interaction between the two kinds of reagents is based on a charge transfer between the reagents.

12. The method for detecting a target nucleic acid according to claim 11, wherein one of the two kinds of the reagents is an electron donor and the other is an electron acceptor.

13. The method for detecting a target nucleic acid according to claim 11, wherein the charge transfer is conducted through the stacking of the base pairs of the double helix of the nucleic acids formed as the result of the formation of the hybrid of the target nucleic acid and the probe.

14. The method for detecting a target nucleic acid according to claim 11, wherein the irreversible change is detected by the change in an electron spin resonance spectrum based on the donation or acceptance of electrons.

15. The method for detecting a target nucleic acid according to claim 1, wherein at least one of the two kinds of the reagents is an intercalator to the bases of the nucleic acid forming the double helix structure.

16. The method for detecting a target nucleic acid according to claim 1, wherein at least one of two kinds of the reagents is covalently bonded to the probe.

17. A kit for detecting a single stranded target nucleic acid, comprising
   a probe having a complementary base sequence to that of the target nucleic acid to form a double-stranded hybrid;
   first and second reagents, both of which being capable of interacting with each other through the hybrid without direct physical contact between the reagents to cause an irreversible, detectable change in at least one of the reagents; and
   a reactor for hybridizing the target with the probe, the reactor being capable of controlling a temperature of a sample containing the target, the probe and the first and the second reagents so as to cause repeated formation and dissociation of the double-stranded hybrid to generate an interaction between the two reagents through the hybrid which results in accumulation of irreversibly changed reagent which provides the detectable change.

18. A method for detecting a target nucleic acid which comprises:
   (a) providing a sample containing a single stranded target nucleic acid having a specific base sequence;
   (b) providing a probe having a base sequence complementary to the specific base sequence and having a first and a second reagent bound to both ends of the probe, the reagents being capable of interacting with each other through a double-stranded nucleic acid which is formed between the probe and the target nucleic acid;
   (c) forming a double-stranded hybrid between the target nucleic acid and the probe to interact the reagents with each other and causing an irreversible detectable change in at least one of the reagents by the interaction;
   (d) causing repeated formation and dissociation of the double stranded hybrid to generate the interaction between the two kinds of reagents which results in accumulations of irreversibly changed reagent which provides the detectable change; and
   (e) detecting the change provided from the accumulated irreversibly changed reagent to ascertain nucleic acid in the sample.

19. The method according to claim 18, wherein the first reagent is an electron donor and the second reagent is an electron acceptor.

20. The method according to claim 19, wherein the electron acceptor is a spin labeling agent containing spins which are decoupled irreversibly when the spin labelling agent receives charges.

21. The method according to claim 20, wherein the step (e) is conducted by detecting a signal representing a quantity of the spin labeling agent whose spins are decoupled.

22. The method according to claim 20, wherein the spin labeling agent is 4-hydroxy-2,2,6,6-tetramethylpiperidine.

23. The method according to claim 19, wherein the electron donor is fluorescein.

24. The method according to claim 19, wherein the probe has at least an 8-base length.

25. A method for detecting a target nucleic acid comprising the steps of:
   (a) providing a sample containing a single stranded target nucleic acid having a specific base sequence;
   (b) providing a probe having a base sequence complementary to the specific base sequence and having a first reagent bound to the probe;
   (c) forming a double-stranded hybrid between the target nucleic acid and the probe in a presence of a second reagent capable of interacting with the first reagent through the double-stranded hybrid without direct physical contact between the two kinds of reagents, to interact the reagents with each other and causing an irreversible detectable change in at least one of the reagents by the interaction;
   (d) causing repeated formation and dissociation of the double stranded hybrid to generate the interaction between the reagents which results in accumulations of irreversibly changed reagent which provides the detectable change; and
   (e) detecting the change provided from the accumulated irreversibly changed reagent to ascertain the target nucleic acid in the sample.

26. The method according to claim 25, wherein the first reagent is an electron donor and the second reagent is an electron acceptor.

27. The method according to claim 26, wherein the electron acceptor is a spin labeling agent containing spins which are decoupled irreversibly when the spin labelling agent receives charges.

28. The method according to claim 27, wherein the step (e) is conducted by detecting a signal representing a quantity of the spin labeling agent whose spins are decoupled.

29. The method according to claim 27, wherein the spin labeling agent is 4-hydroxy-2,2,6,6-tetramethylpiperidine.

30. The method according to claim 26, wherein the electron donor is fluorescein.

* * * * *

UNITED STATES PATENT AND TRADEMARK OFFICE
CERTIFICATE OF CORRECTION

PATENT NO. : 5,705,346

DATED : January 6, 1998

INVENTOR(S): TADASHI OKAMOTO ET AL.

Page 1 of 3

It is certified that error appears in the above-identified patent and that said Letters Patent is hereby corrected as shown below:

ON THE TITLE PAGE AT [56] References Cited
   OTHER PUBLICATIONS, After "Cardullo et al.": "nonradiatibe"
     should read --nonradiative--;
   After "Cullis et al.": "Electorn" should read --Electron--.

COLUMN 2
   Line 15, "problems." should read --problems:--;
   Line 17, "the" should be deleted;
   Line 18, "the" (both occurrences) should be deleted;
   Line 25, "owing" should read --owing to--.

COLUMN 3
   Line 48, "nuclei" should read --nucleic--.

COLUMN 5
   Line 22, "molecular" should be deleted.

COLUMN 6
   Line 66, "single stranded" should read --single-stranded--.

COLUMN 7
   Line 24, "the electric" should read --electric--;
   Line 35, "straight streams" should read --streams
     straight--.

COLUMN 10
   Line 43, "gas tight" should read --gas-tight--;
   Line 56, "tective" should read --tective group--;
   Line 62, "(0.2$\mu$M," should read --(0.2 pM,--.

UNITED STATES PATENT AND TRADEMARK OFFICE
CERTIFICATE OF CORRECTION

PATENT NO. : 5,705,346

DATED : January 6, 1998

INVENTOR(S): TADASHI OKAMOTO ET AL.

It is certified that error appears in the above-identified patent and that said Letters Patent is hereby corrected as shown below:

COLUMN 12
   Line 43, "gas tight" should read --gas-tight--.

COLUMN 13
   Line 17, "targe" should read --target--;
   Line 20, "targe" should read --target--.

COLUMN 15
   Line 9, "single stranded" should read --single-stranded--;
   Line 21, "double stranded" should read --double-stranded--;
   Line 35, "of that in" should read --in which--;
   Line 35, "double" should read --double---;
   Line 37, "of the double stranded" should read --in which the double-stranded--.

COLUMN 16
   Line 22, "single stranded" should read --single-stranded--;
   Line 23, "comprising" should read --comprising:--;
   Line 42, "single stranded" should read --single-stranded--;
   Line 56, "double stranded" should read --double-stranded--.

COLUMN 17
   Line 1, "labelling" should read --labeling--;
   Line 14, "single stranded" should read --single-stranded--.

UNITED STATES PATENT AND TRADEMARK OFFICE
CERTIFICATE OF CORRECTION

PATENT NO. : 5,705,346

DATED : January 6, 1998

INVENTOR(S): TADASHI OKAMOTO ET AL.

It is certified that error appears in the above-identified patent and that said Letters Patent is hereby corrected as shown below:

COLUMN 18
```
  Line 2  "double stranded" should read --double-stranded--;
  Line 15, "labelling" should read --labeling--.
```

Signed and Sealed this

Eighteenth Day of August, 1998

Attest:

BRUCE LEHMAN

Attesting Officer

Commissioner of Patents and Trademarks